United States Patent
Baynham et al.

(10) Patent No.: US 8,083,799 B2
(45) Date of Patent: Dec. 27, 2011

(54) SPINAL IMPLANT

(75) Inventors: Bret O. Baynham, Jupiter, FL (US); G. Clay Baynham, Jupiter, FL (US); David R. Campbell, Jupiter, FL (US); Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 887 days.

(21) Appl. No.: 12/109,896

(22) Filed: Apr. 25, 2008

(65) Prior Publication Data
US 2008/0275506 A1    Nov. 6, 2008

Related U.S. Application Data

(63) Continuation-in-part of application No. 11/741,249, filed on Apr. 27, 2007.

(51) Int. Cl.
*A61F 2/44* (2006.01)
(52) U.S. Cl. .................... 623/17.16; 606/246
(58) Field of Classification Search ..... 623/17.11–17.16
See application file for complete search history.

(56) References Cited

U.S. PATENT DOCUMENTS

| | | | |
|---|---|---|---|
| 4,016,863 A | 4/1977 | Brantigan | |
| 4,349,921 A * | 9/1982 | Kuntz | 623/17.16 |
| 4,743,256 A | 5/1988 | Brantigan | |
| 4,834,757 A | 5/1989 | Brantigan | |
| 4,878,915 A | 11/1989 | Brantigan | |
| 5,015,247 A | 5/1991 | Michelson | |
| 5,192,327 A | 3/1993 | Brantigan | |
| 5,425,772 A | 6/1995 | Brantigan | |
| 5,645,598 A | 7/1997 | Brosnahan, III | |
| 5,658,336 A * | 8/1997 | Pisharodi | 623/17.16 |
| 5,665,122 A | 9/1997 | Kambin | |
| 5,766,253 A | 6/1998 | Brosnahan, III | |
| 5,865,847 A | 2/1999 | Kohrs et al. | |
| 5,888,222 A * | 3/1999 | Coates et al. | 623/17.16 |
| 6,080,158 A * | 6/2000 | Lin | 606/247 |
| 6,090,143 A | 7/2000 | Meriwether et al. | |
| 6,096,080 A | 8/2000 | Nicholson et al. | |
| 6,102,948 A | 8/2000 | Brosnahan, III | |
| 6,123,705 A | 9/2000 | Michelson | |
| 6,149,686 A | 11/2000 | Kuslich et al. | |
| 6,159,245 A | 12/2000 | Meriwether et al. | |
| 6,224,595 B1 | 5/2001 | Michelson | |
| 6,241,733 B1 | 6/2001 | Nicholson et al. | |
| 6,241,769 B1 | 6/2001 | Nicholson et al. | |
| 6,258,094 B1 | 7/2001 | Nicholson et al. | |
| 6,261,293 B1 | 7/2001 | Nicholson et al. | |
| 6,261,295 B1 | 7/2001 | Nicholson et al. | |
| 6,267,763 B1 | 7/2001 | Castro | |

(Continued)

*Primary Examiner* — Thomas C. Barrett
*Assistant Examiner* — Jerry Cumberledge
(74) *Attorney, Agent, or Firm* — McHale & Slavin, P.A.

(57) ABSTRACT

A spinal implant for insertion in the intervertebral space is formed as a hollow cage, wedge shaped in profile, with a lesser height leading end for a low profile entry. The cage has two open sides with a plurality of angled teeth along opposite longitudinal edges for engaging the end plates of adjacent vertebrae when the cage is rotated into position. One portion of the angled teeth is angled toward an end of the cage and another portion of the angled teeth is angled away from that end to provide a lock preventing the cage from migrating ventrally or dorsally from the spine. Upon rotation, the leading end has a greater height than the trailing end. Opposing side walls of the cage include recesses to facilitate rotation of the cage and minimize stress on adjacent vertebrae.

13 Claims, 13 Drawing Sheets

U.S. PATENT DOCUMENTS

| | | |
|---|---|---|
| 6,290,724 B1 | 9/2001 | Marino |
| 6,312,431 B1 | 11/2001 | Asfora |
| 6,488,710 B2 | 12/2002 | Besselink |
| 6,530,955 B2 | 3/2003 | Boyle et al. |
| 6,576,016 B1 | 6/2003 | Hochshuler et al. |
| 6,582,431 B1 | 6/2003 | Ray |
| 6,666,889 B1 * | 12/2003 | Commarmond ............ 623/17.11 |
| 6,679,887 B2 | 1/2004 | Nicholson et al. |
| 6,743,255 B2 | 6/2004 | Ferree |
| 6,746,484 B1 | 6/2004 | Liu et al. |
| 6,767,366 B2 * | 7/2004 | Lee et al. .................... 623/17.16 |
| 6,800,093 B2 | 10/2004 | Nicholson et al. |
| 6,805,697 B1 | 10/2004 | Helm et al. |
| 6,827,743 B2 | 12/2004 | Eisermann et al. |
| 6,942,697 B2 | 9/2005 | Lange et al. |
| 7,018,412 B2 * | 3/2006 | Ferreira et al. ............. 623/17.11 |
| D524,443 S | 7/2006 | Blain |
| 7,135,043 B2 * | 11/2006 | Nakahara et al. .......... 623/17.11 |
| 7,169,183 B2 | 1/2007 | Liu et al. |
| 7,320,686 B2 | 1/2008 | Serhan et al. |
| 7,588,599 B2 | 9/2009 | Sweeney |
| 2002/0032483 A1 | 3/2002 | Nicholson et al. |
| 2002/0123750 A1 | 9/2002 | Eisermann et al. |
| 2003/0023306 A1 | 1/2003 | Liu et al. |
| 2003/0097136 A1 | 5/2003 | Hajianpour |
| 2003/0153975 A1 | 8/2003 | Byrd, III et al. |
| 2003/0232065 A1 | 12/2003 | Remington et al. |
| 2003/0233147 A1 | 12/2003 | Nicholson et al. |
| 2004/0006125 A1 | 1/2004 | Remington et al. |
| 2004/0186572 A1 | 9/2004 | Lange et al. |
| 2004/0215202 A1 | 10/2004 | Preissman |
| 2005/0038514 A1 | 2/2005 | Helm et al. |
| 2005/0043733 A1 | 2/2005 | Eisermann et al. |
| 2005/0070900 A1 | 3/2005 | Serhan et al. |
| 2005/0119747 A1 | 6/2005 | Monterumici et al. |
| 2005/0246021 A1 | 11/2005 | Ringeisen et al. |
| 2005/0273166 A1 | 12/2005 | Sweeney |
| 2006/0167548 A1 * | 7/2006 | Jackson ..................... 623/17.11 |
| 2006/0217806 A1 | 9/2006 | Peterman |
| 2006/0247771 A1 | 11/2006 | Peterman |
| 2007/0050031 A1 | 3/2007 | Khosrowshahi |
| 2007/0093898 A1 | 4/2007 | Schwab |
| 2007/0270956 A1 * | 11/2007 | Heinz ........................ 623/17.11 |
| 2008/0288076 A1 | 11/2008 | Soo et al. |
| 2009/0312837 A1 * | 12/2009 | Eisermann et al. ........ 623/17.11 |

* cited by examiner

SPINAL IMPLANT

PRIORITY CLAIM

This application is a continuation-in-part of application Ser. No. 11/741,249 filed on Apr. 27, 2007 entitled Spinal Implant, the contents of which are hereby expressly incorporated herein by reference.

BACKGROUND OF THE INVENTION

1. Field of the Invention

This invention relates to spinal implants inserted between adjacent vertebrae to stabilize the intervertebral space and correct the angle of the spine. The implant also facilitates fusion of the affected vertebrae.

2. Description of the Prior Art

The spinal cage is a well known device for insertion between vertebrae to provide support in lieu of the natural spinal disc. The cages may be of different shapes, including rectangle, cylinder and wedge, enclosing an interior filled with bone growth material, among other compositions, which promote the fusion of the vertebrae on each side of the cage. The cages are open structures which allow vascularization and bone in-growth.

It is very important that these cages be prevented from migrating out of the prepared surgical site because any movement will prolong the fusion process and traumatize healthy tissue.

U.S. Pat. No. 6,746,484 B1 to Liu et al illustrates such a wedge shaped cage with rectilinear ends. Liu et al is directed to proper placement of the cage so that the large and small ends of the wedge are support members and the interconnected sides facilitate fusion or bone growth. Distractors with screw-like threads are used to form a shaped bed in the end plates of the adjacent vertebrae to accept the cage. The cage has two open opposite long sides and two closed long sides. The filled cage is inserted into the prepared site and rotated 90 degrees so that the open sides will be in contact with the end plates of the adjacent vertebrae. The cage is held in place by compression between the vertebrae.

U.S. Pat. No. 5,425,772 to Brantigan is directed to another wedge shaped implant similar to the cage described above. The surgical site is prepared by cutting slots in the adjacent vertebrae end plates and separating the end plates by distraction. The closed long sides have a series of sharpened ridges or teeth extending across the closed sides parallel to the ends. The teeth are shaped as elongated isosceles triangles for biting into the adjacent vertebrae surfaces when implanted. The valleys between the teeth are filled with bone growth material to promote fusion. After implantation, the distraction is released to reduce the space between the vertebrae and to seat the implant by compression.

What is lacking in the prior art is a spinal cage which has a large open vertebral contact area for boney in-growth and a locking structure to prevent ventral and dorsal movement after implantation and a cage that can provide lordosis, mimicking the natural curvature of the spine.

SUMMARY OF THE PRESENT INVENTION

Therefore, an object of this invention is to provide a spinal implant sized and shaped to support adjacent vertebrae in the proper angular and spatial relationship.

It is another object of this invention to provide a spinal implant cage with a hollow interior to serve as a reservoir of bone growth material and to provide a large contact area between the material and the vertebrae.

It is a further object of this invention to provide a plurality of angled teeth securing the cage to the end plates of the vertebrae and preventing migration of the implant from the implant site.

It is yet another object of this invention to provide a method of implanting the cage by rotation of the cage to engage the angled teeth in the end plates of the vertebrae.

It is a still further object of this invention to provide a wedge shape in which the major distraction distance shifts from the trailing end to the leading end as the cage is rotated.

It is still yet an object of this invention to provide a method of facilitating the rotation of the cage by providing a recessed surface areas along the elongated side walls to minimize the stress placed on adjacent vertebrae as the cage is rotated.

It is further still yet an object of this invention to provide a stop plate to prevent over rotating the cage to an undesirable position.

SHORT DESCRIPTION OF THE DRAWINGS

DETAILED DESCRIPTION OF THE INVENTION

Figure 1:
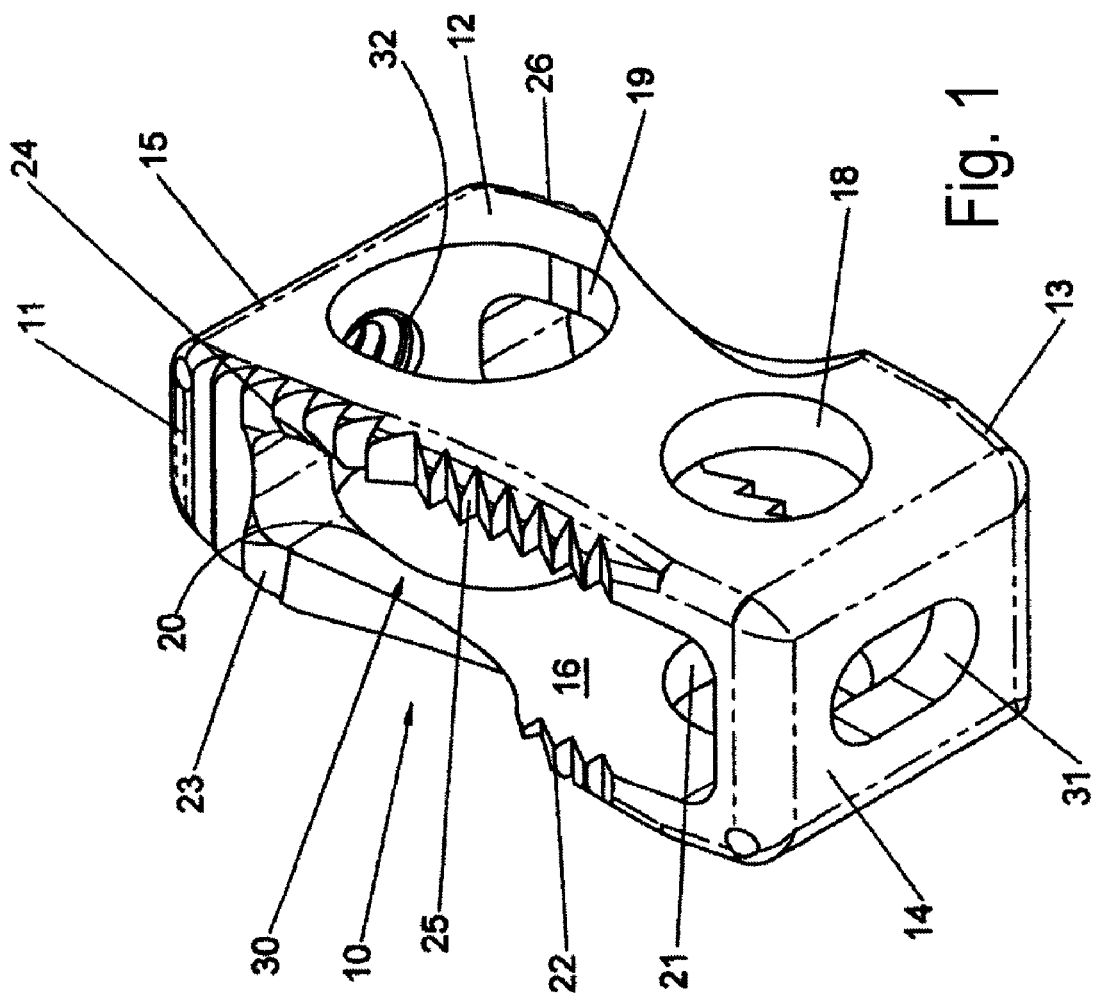
FIG. 1 is a perspective view of the spinal cage of this invention.
Figure 2:
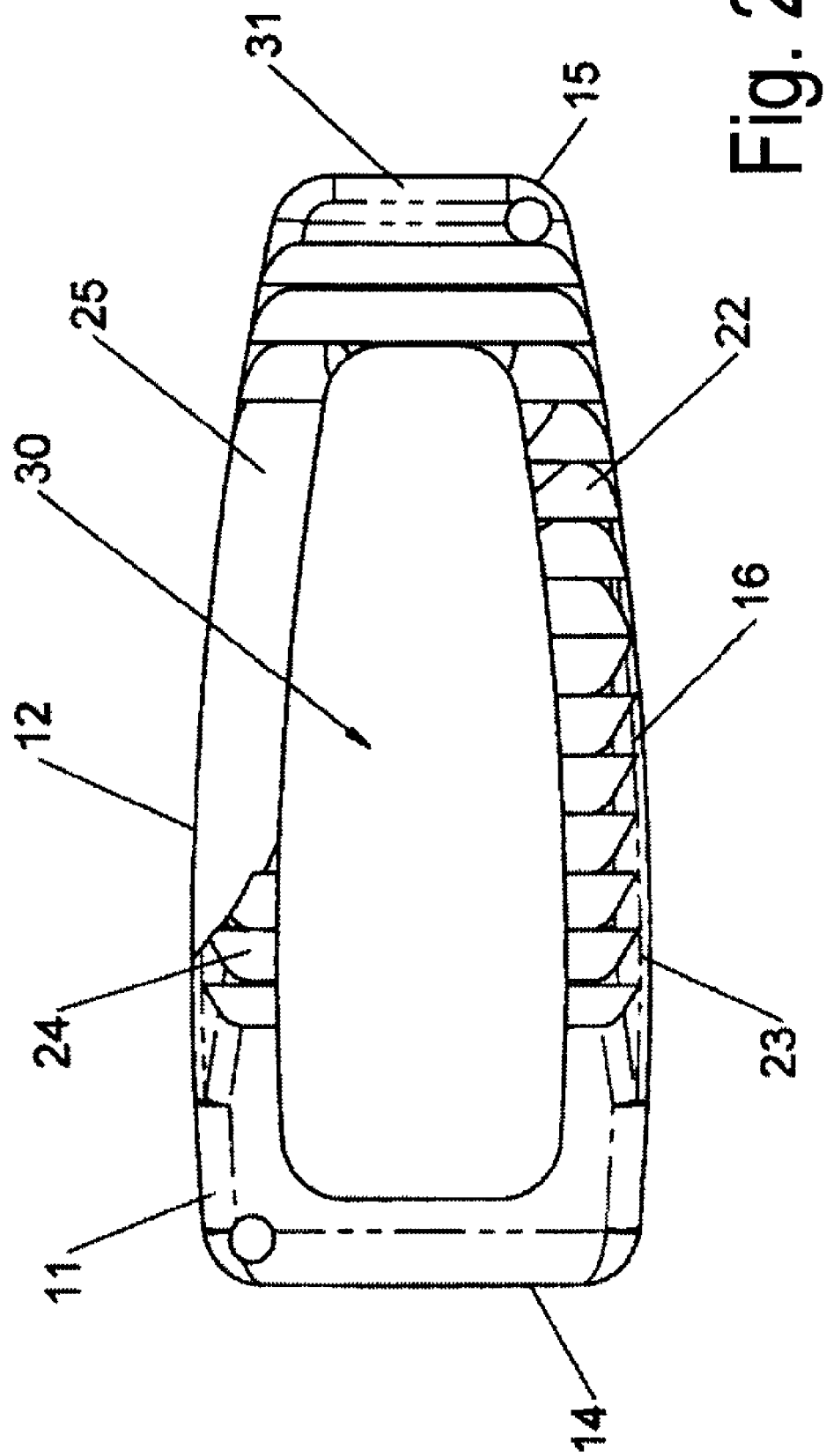
FIG. 2 is a top plan view of the cage of FIG. 1.
Figure 3:
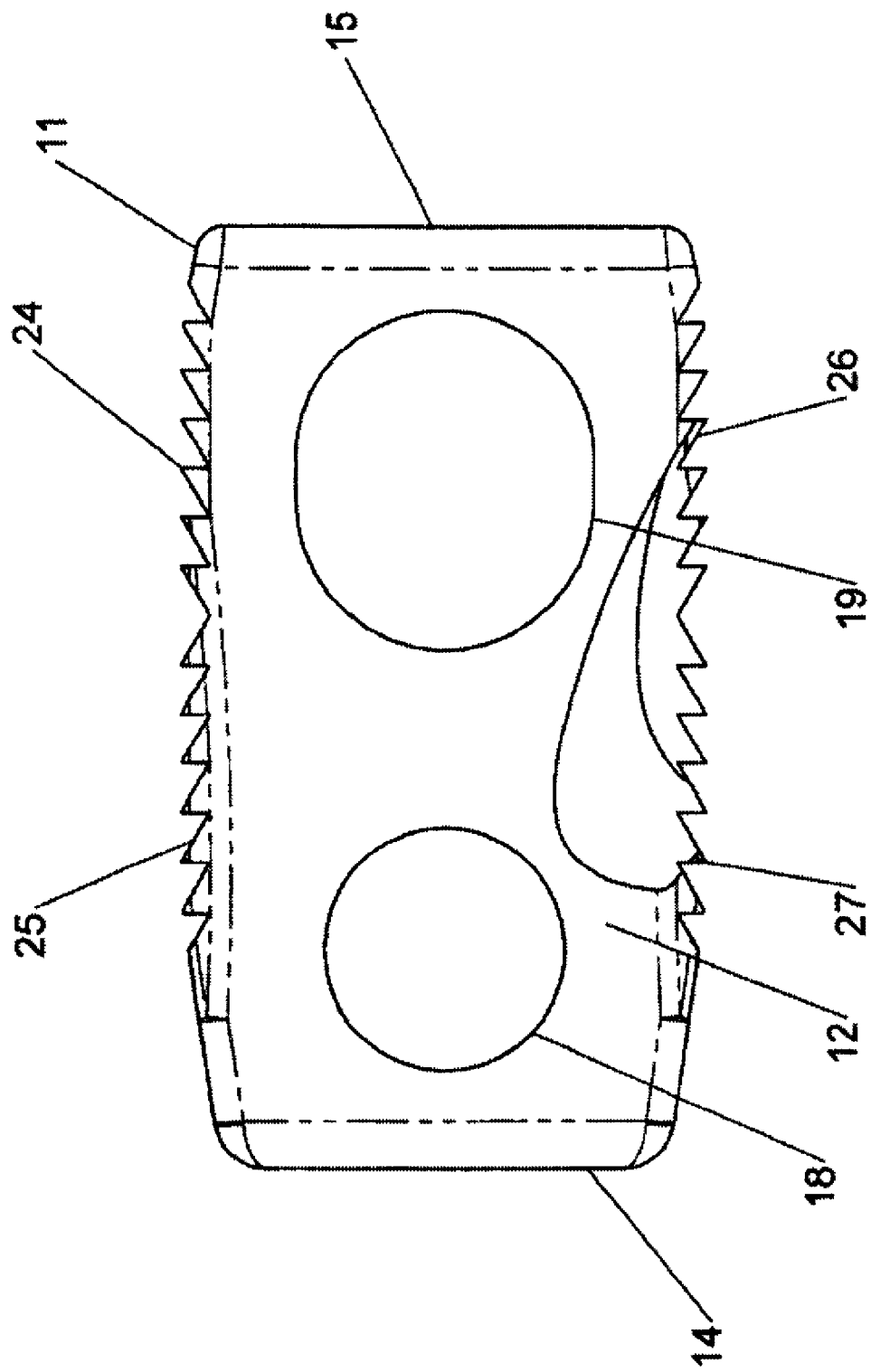
FIG. 3 is a side plan view of the cage of FIG. 1.
Figure 4:
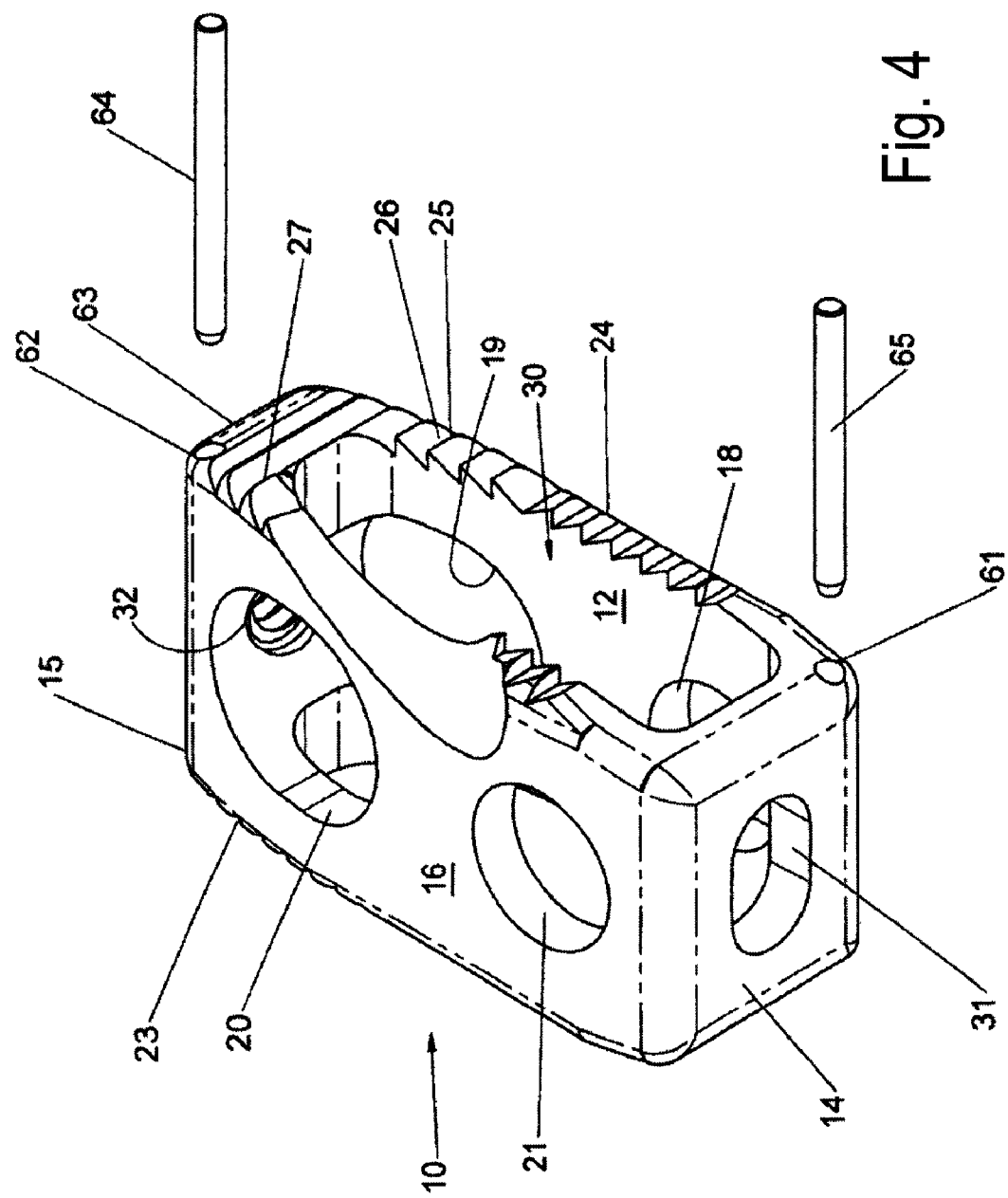
FIG. 4 is an exploded perspective of another embodiment of the cage of this invention.

The spinal implant is formed as a cage 10 with a hollow interior 30, as shown in FIG. 1, surrounded by an open framework. The cage shown in FIGS. 1, 2, and 3 has an overall shape of a wedge with a smaller end wall 14 and a larger end wall 15. As shown in FIGS. 1 and 4, the leading end 15 is longer than trailing end 14. Elongated sidewalls 12 and 16 connect the ends and are disposed diametrically opposite to each other. Sidewall 12 has apertures 18 and 19 which communicate with the interior 30. Sidewall 16 is a mirror image of sidewall 12 and includes apertures 20 and 21. The apertures in the sidewalls may be the same size or different sizes, as shown. The apertures contribute to the integration of the implant into spine. The cage may be made of surgical stainless steel, titanium, other metallic alloys, ceramics, polymeric material or combinations thereof that are bio-compatible and have sufficient strength to support adjacent vertebrae in desired spatial relationship with proper curvature of the spine.

Along the longitudinal periphery of the sidewall 12 is a series of teeth terminating in a sharpened apex. On one portion of the periphery the teeth 24 and 26 are angled away from the small end 14. In the other portion of the periphery of sidewall 12, the teeth 25 and 27 are angled toward the small end wall 14, as shown in FIG. 3. The periphery of sidewall 16 is similarly shaped with the teeth 22 angled away from the small end wall 14 and the teeth 23 angled toward the small end wall 14. The angled teeth gain purchase in the bone and act as a ratchet to prevent relative movement between the implant and the end plates of the adjacent vertebrae. The opening 30 between the periphery of side walls 12 and 16 communicates with the hollow interior of the cage. When the cage is filled with bone growth and/or other material, this large opening on either side of the cage provides a large contact area to promote boney in growth, vascularization and fusion of the adjacent vertebrae.

The end smaller wall 14, shown in FIG. 1, has an oblong opening 31 which mates with an implant tool (not shown) used to manipulate the implant for permanent positioning in the spine. The longer end wall 15 has a threaded opening 32 opposite the opening 31 to which the implant tool may be removably connected. These openings, 31 and 32, may be reversed.

The manipulation would normally include insertion through a percutaneous opening in the patient's back and sliding the implant into a prepared site between lumbar vertebrae. The longer end wall 15 is the leading end with the smooth width of one of the sidewalls contacting the upper vertebrae and the other sidewall contacting the lower vertebrae. To this end, the sidewalls 12 and 16 are bowed outwardly in an arc increasing the volume of the hollow interior and reducing the area of sliding contact with the vertebral end plates. Also, the end walls 14 and 15 may be rectilinear with the sidewalls connecting the opposite sides of the rectangles so that the implant has a low profile during insertion within the prepared spinal site. The low profile leading end is shown in the insertion phase in FIG. 2.

Once within the spinal site, the implant is rotated approximately 90 degrees to orient the width of the sidewalls of the implant more or less parallel with the longitudinal axis of the spine and engage the teeth with the end plates of the adjacent vertebrae. The rotation results in increasing the profile of the cage at the leading end and reducing the profile at the trailing end, as shown by a comparison of FIG. 2 and FIG. 3.

The implant tool is then removed. The hollow interior 30 of the cage may then be filled with a composition including bone growth material, bone cement, bone particles, and other structural or pharmaceutical components, alone or in combination. In the alternative, the interior of the cage may be filled with the desired material before insertion into the patient. In the final position, the bone growth material is in contact with the end plates of the vertebrae through the large openings on both sides of the implant.

FIG. 4 illustrates another embodiment of the cage which may have a rectilinear shape and radiopaque markers useful during the surgical implantation to locate the forward and rear ends of the cage in relation to the spine for proper placement of the cage. The end walls 14 and 15 each have an opening 61 connecting to a bore 63 along one edge, respectively. Radiopaque rods 64 and 65 are secured in the bores. During the surgical procedure of implantation, the proper positioning of the implant may be monitored by fluoroscope.

Figure 5:
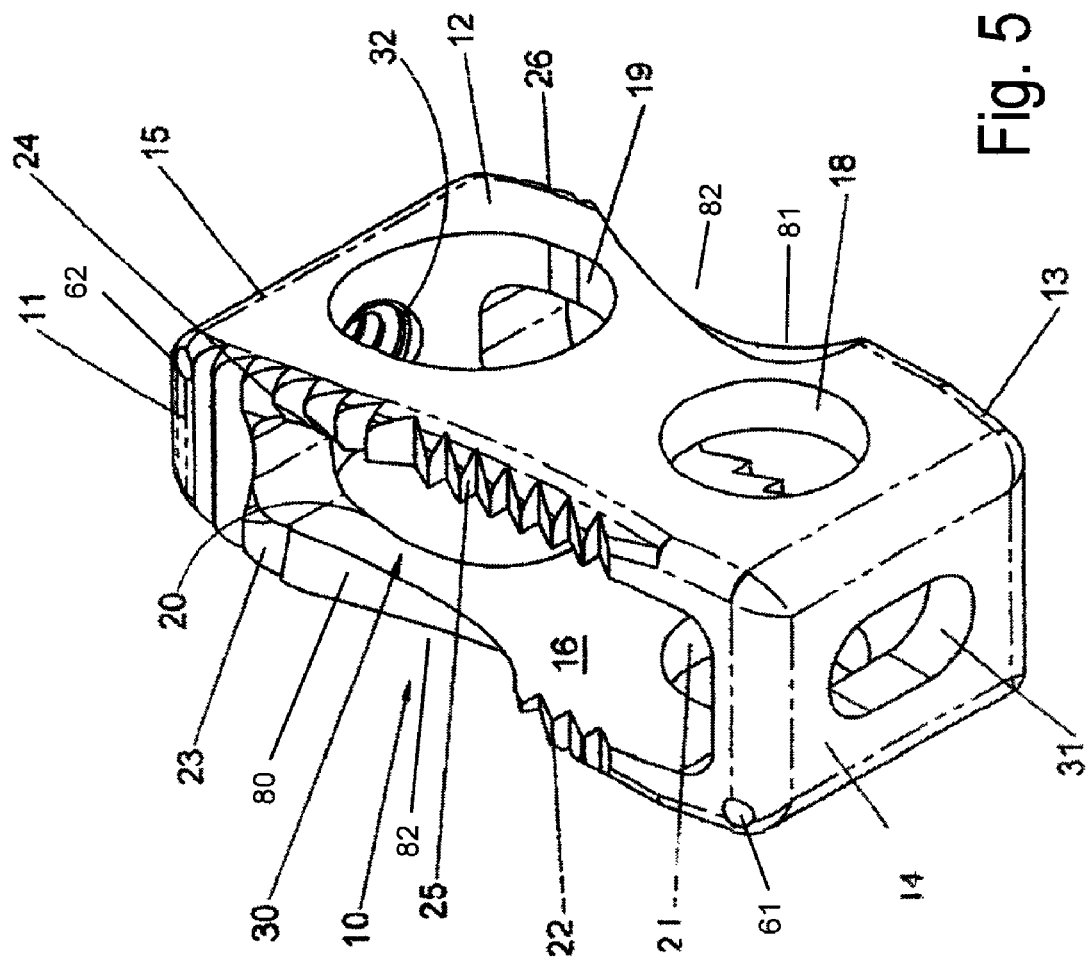
FIG. 5 is a perspective view of another embodiment of the spinal cage of this invention.

With regards to the rotation, the peripheral surfaces of the sidewalls 12 and 16 on top 11 and bottom 13 portion of the cage 10 alternatively includes recesses. FIG. 5 shows first recess 80 and second recess 81. First recess 80, is located on the top portion 11 of the cage 10 and is preferably cut into the exterior surface of the peripheral sidewall 16. The first recess 80 extends from substantially the small end 14 to substantially the large end 15. The second recess 81 is an inverse mirror image of the first recess 80 except on the second recess 81 is located on the bottom portion 13 of the cage 10. More specifically, each recess 80 and 81 includes a pair of opposing faces, defining a carved out open area 82 there between. Because the first recess 80 and the second recess 81 is carved out within the hollow opening 30 the surface area of the opening 82 contains a hollow opening to promote boney in growth, vascularization and fusion of the adjacent vertebrae. The opening 82 may be of a concave, convex, or planar shape. The edge of the recesses preferably slope at an angle of 45 degrees from the centerline CL of the cage, however, it is contemplated that the recesses may vary in angle from 1 degree to 89 degrees from the centerline CL. The recesses are designed to help aid in rotation of the cage. The amount of surface area in contact with the top vertebrae during rotation is decreased with the grooves thus reducing the frictional forces working against the rotation and making the rotation easier. In addition, the spaced traversed between adjacent vertebrae is reduced as the cage is rotated into position thereby minimizing the stress applied to the vertebrae.

Figure 6:
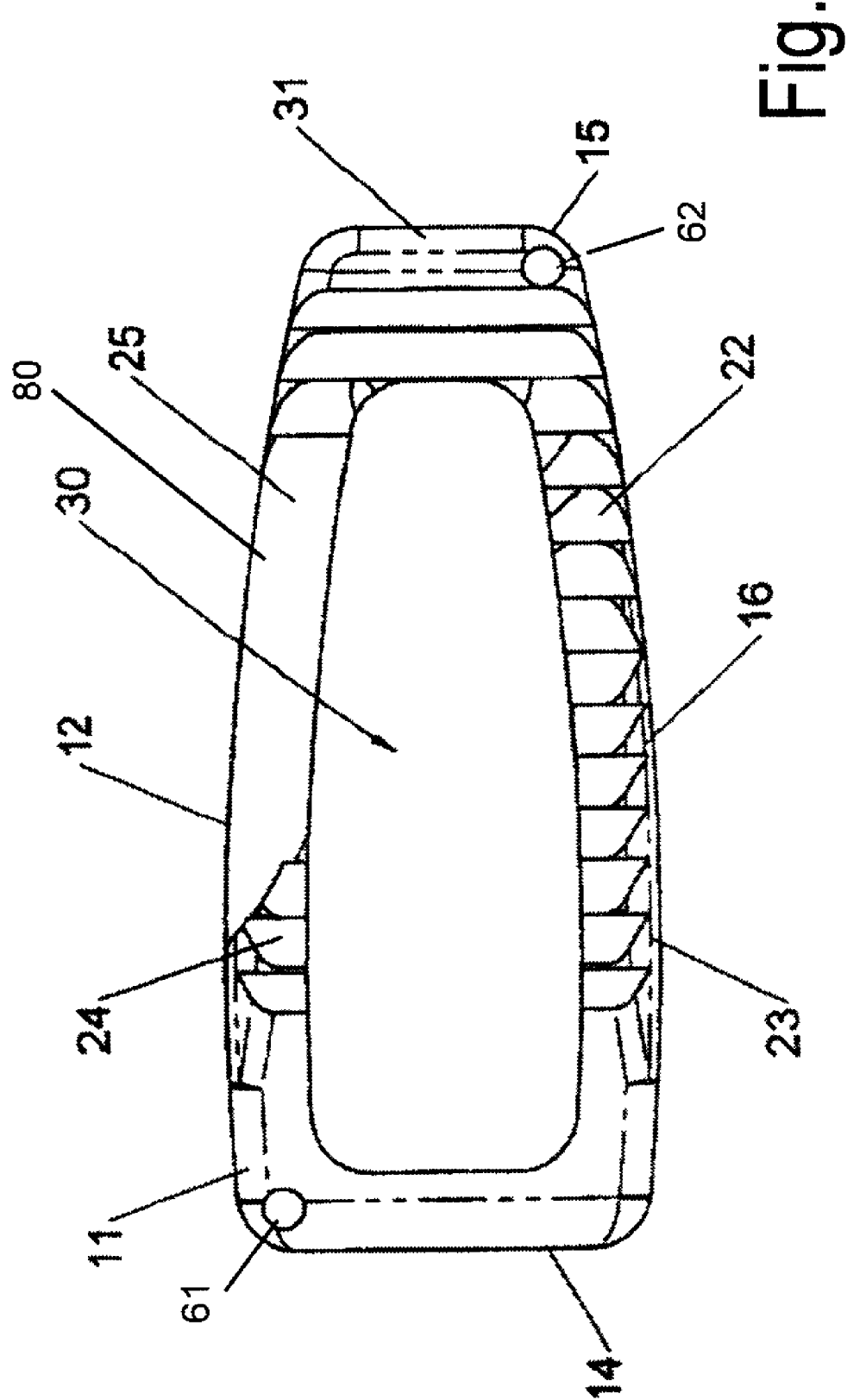
FIG. 6 is a top view of the cage of FIG. 5.

FIG. 6 shows a top view of spinal cage 10 illustrating the groove 81 on elongated side wall 12.

Figure 7:
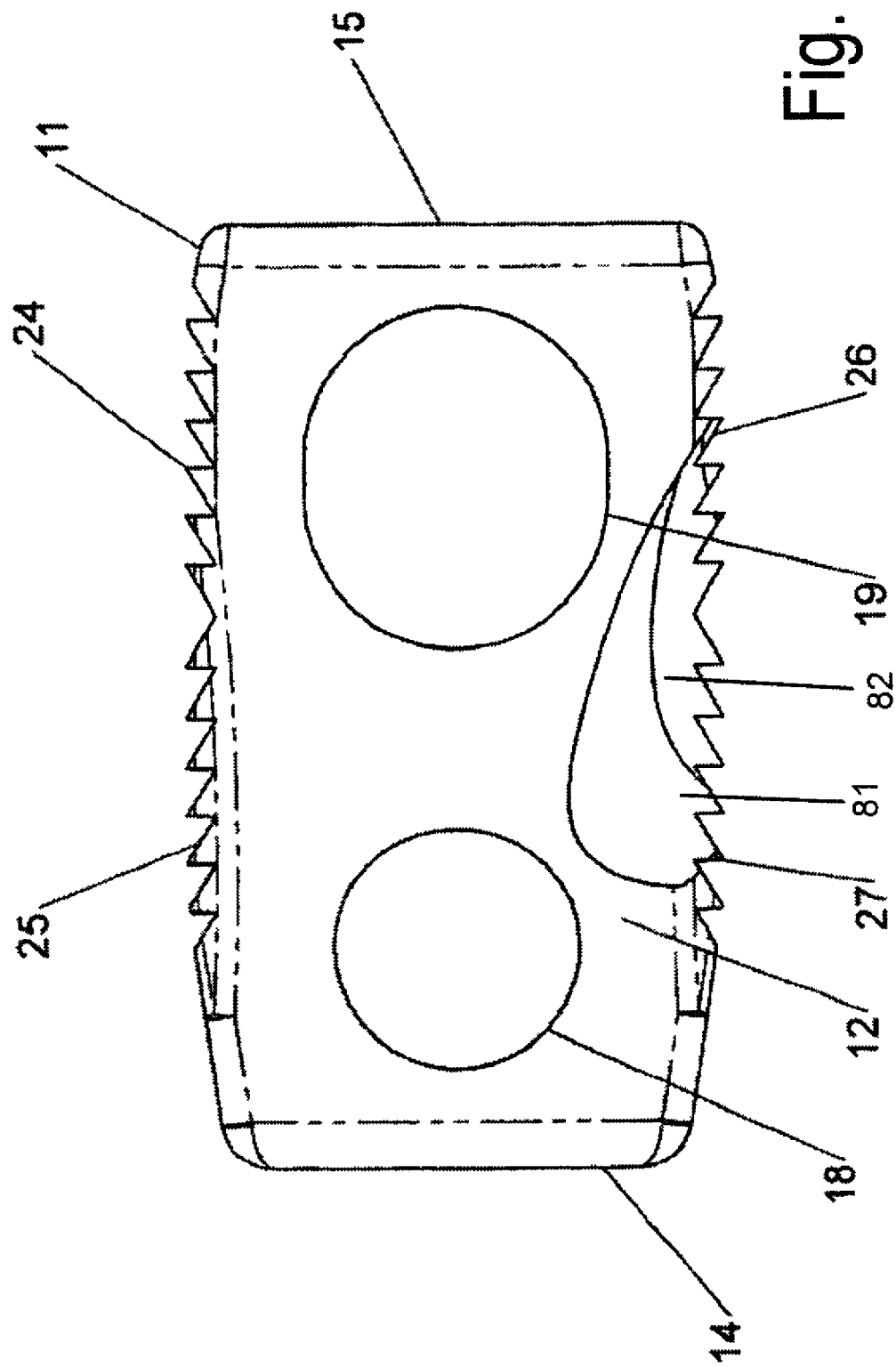
FIG. 7 is a side plan view of the cage of FIG. 5.

FIG. 7 shows a side view of spinal cage 10 illustrating groove 81 and opening 82 on elongated side wall 12.

Figure 8:
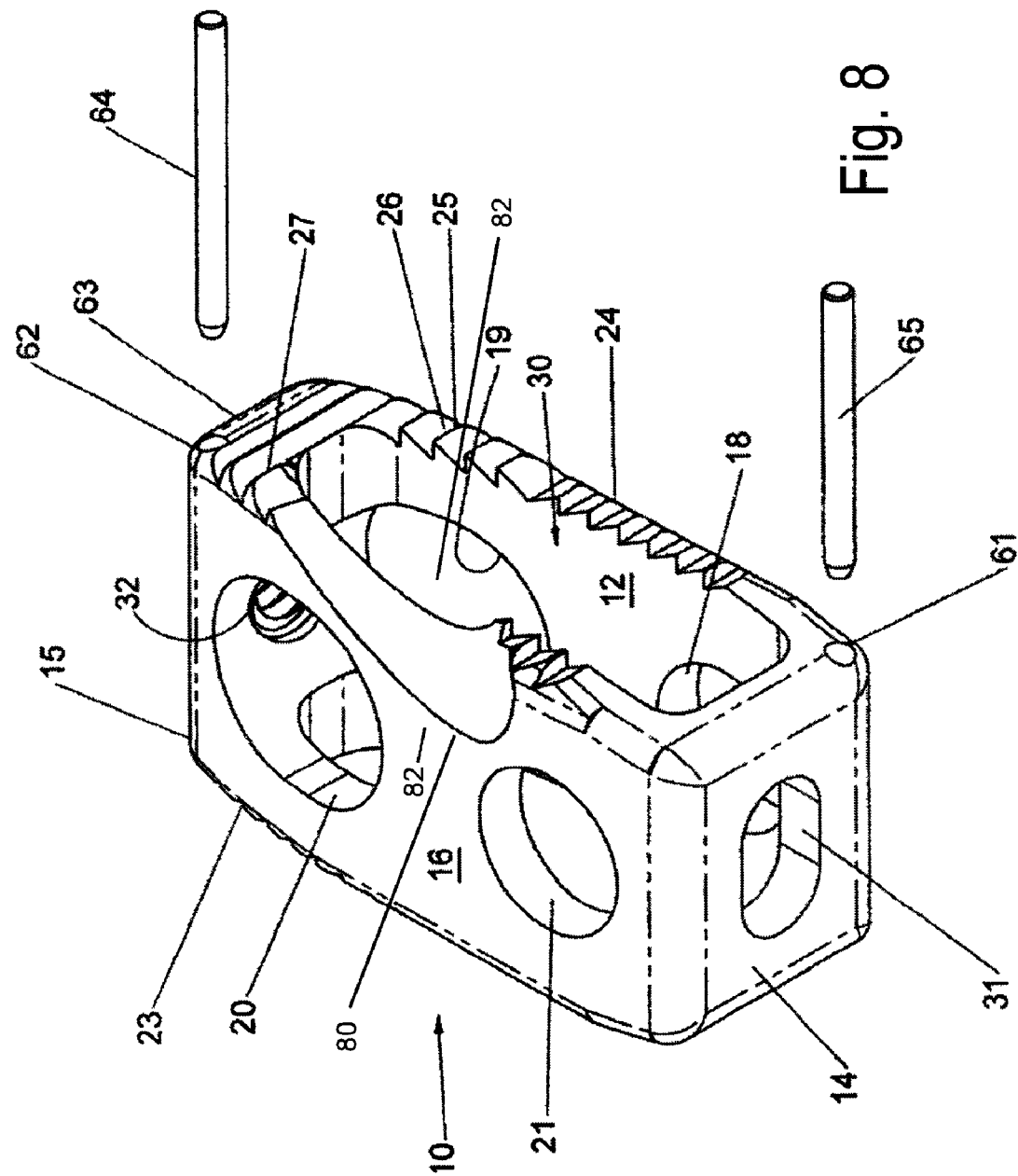
FIG. 8 is a partially exploded view of the spinal cage of FIG. 5 including radiopaque rods.

FIG. 8 shows a partially exploded perspective view of the spinal cage 10 with groove 80 on elongated side wall 16 further including radiopaque markers 64 and 65.

Figure 9:
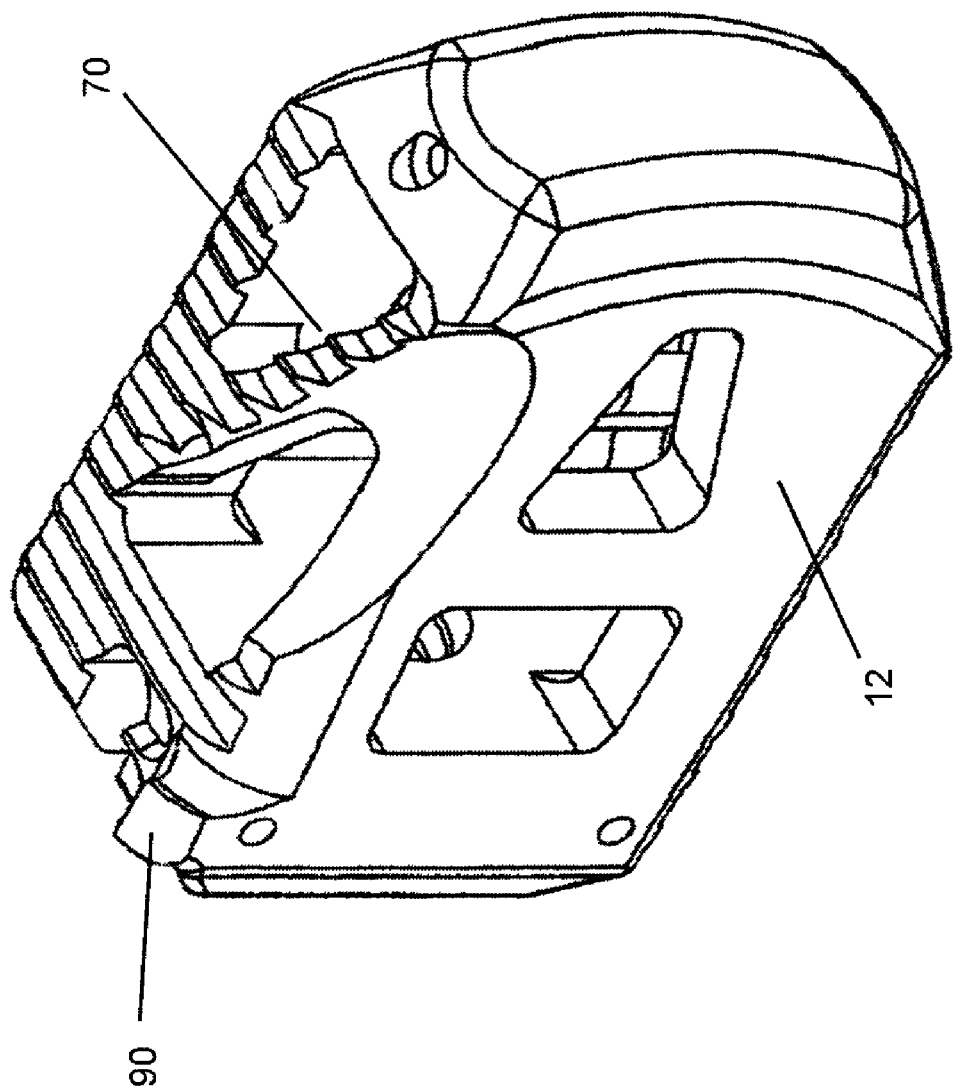
FIG. 9 is a perspective view of another embodiment of the spinal cage invention.
Figure 10:
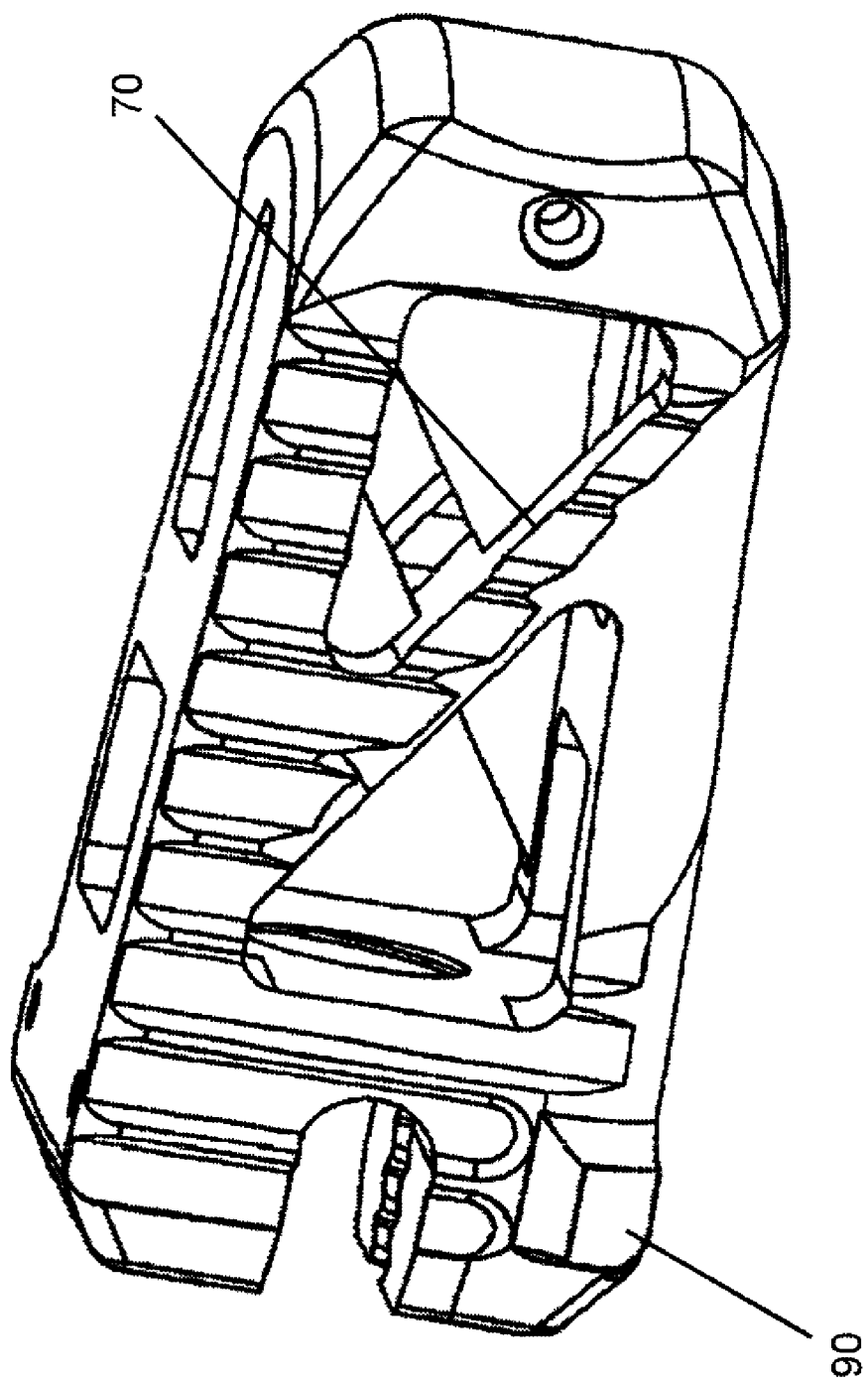
FIG. 10 is a top view of the spinal cage of FIG. 9
Figure 11:
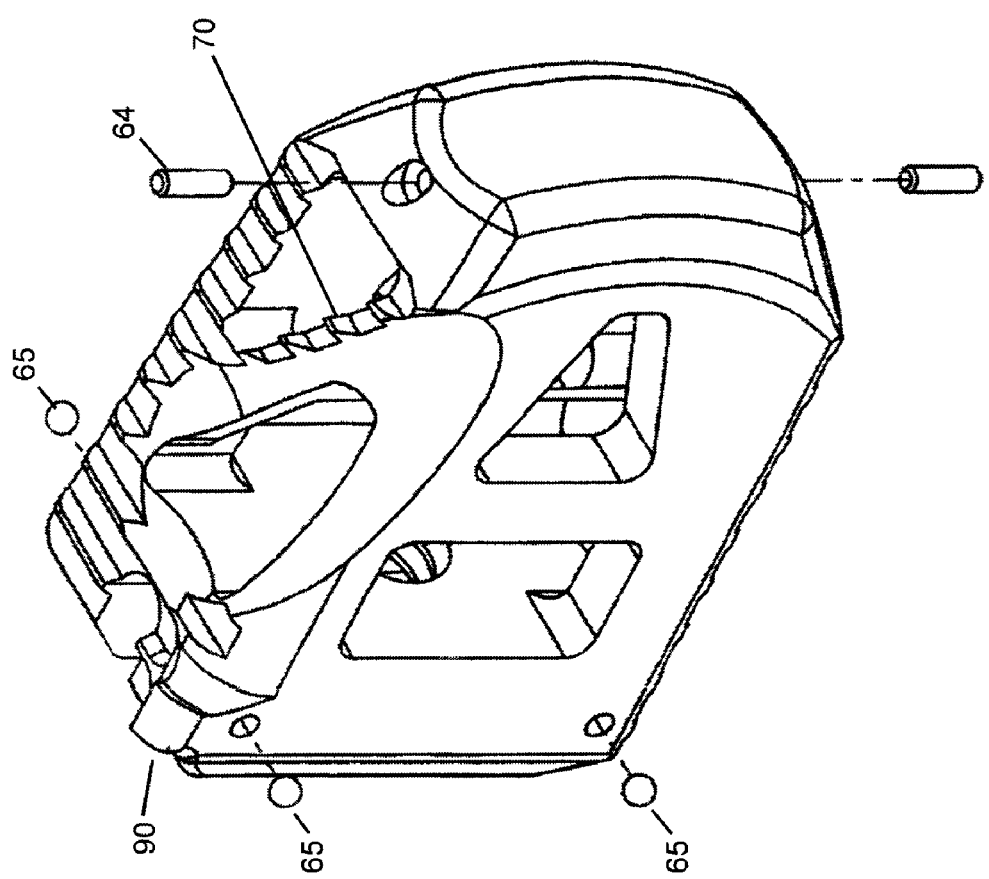
FIG. 11 is a partially exploded view of the spinal cage of FIG. 9 including radiopaque rods.
Figure 13:
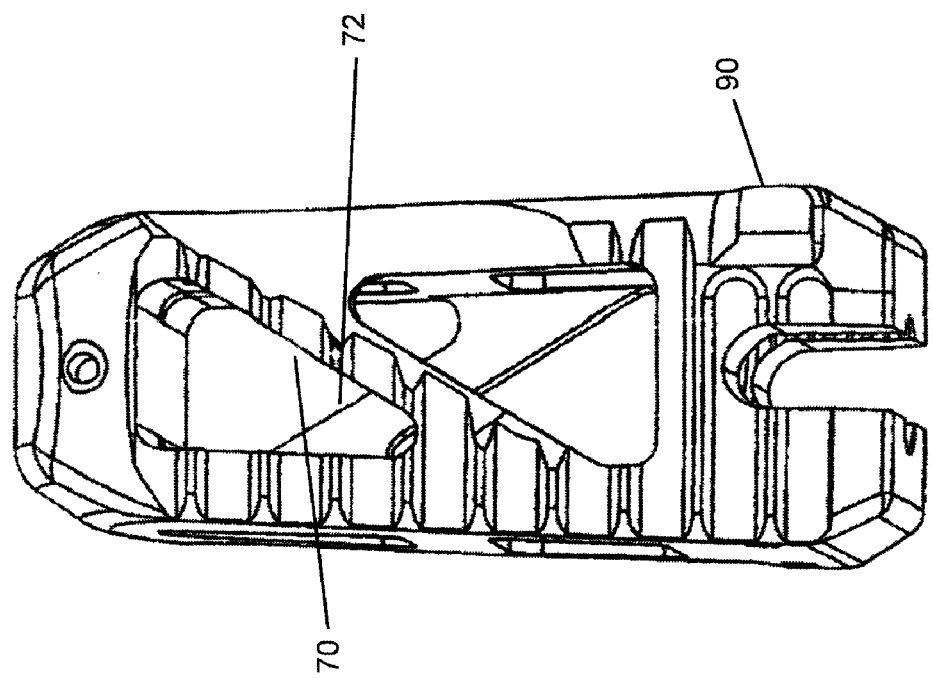
FIG. 13 is another top view of the spinal cage shown in FIG. 9.
Figure 12:
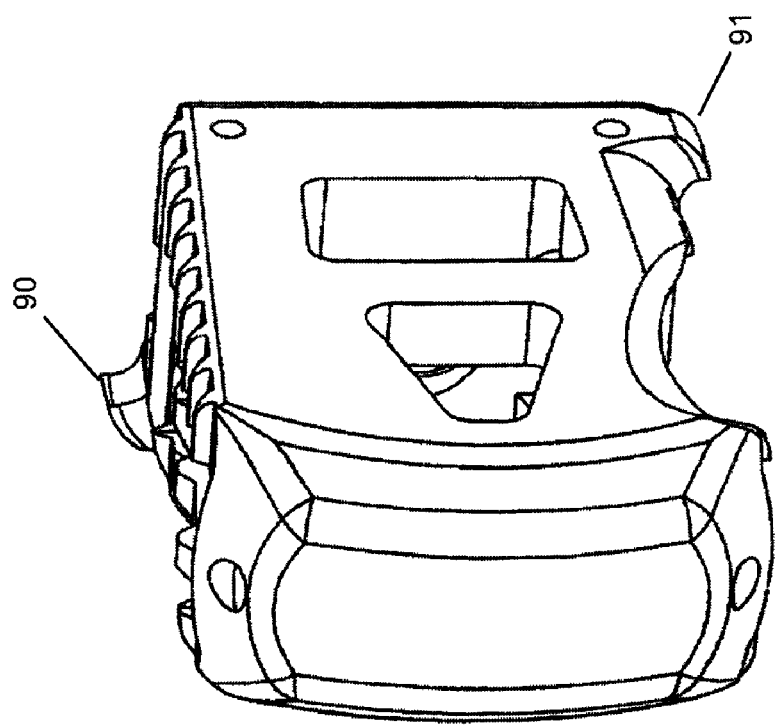
FIG. 12 is another perspective view of the spinal cage shown in FIG. 9.
Figure 15:
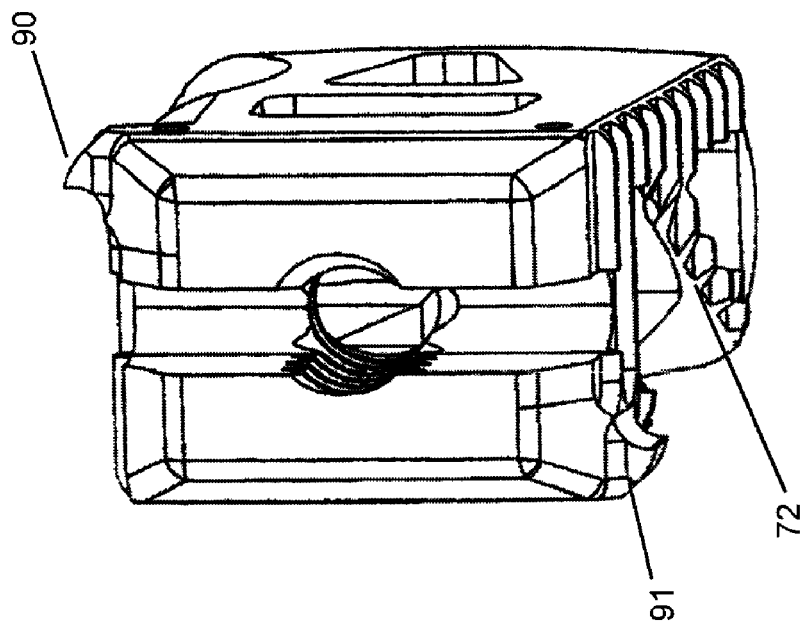
FIGS. 14 and 15 are end views of the spinal cage shown in FIG. 9.
Figure 14:
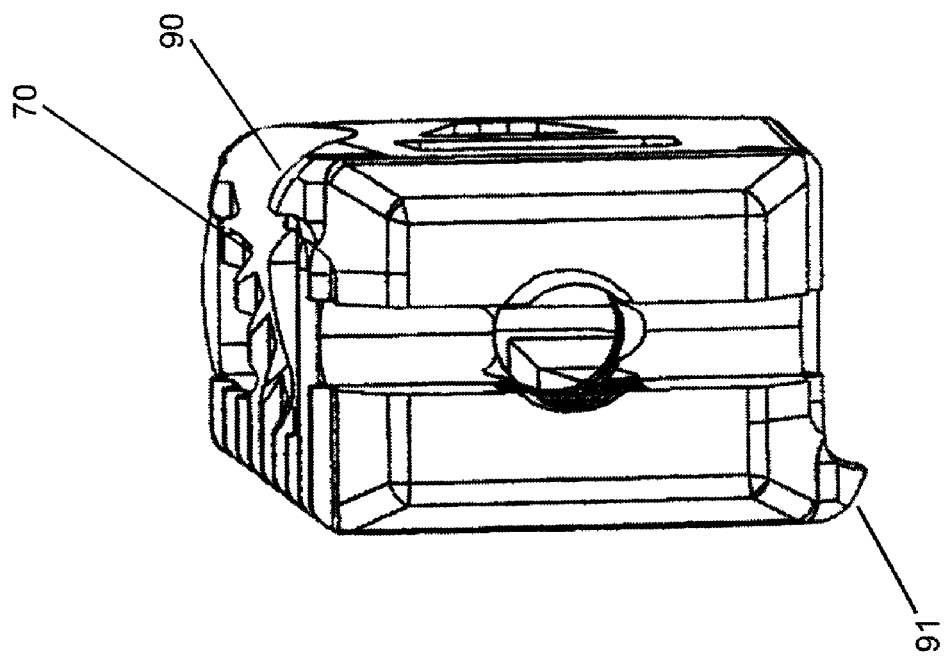

FIGS. 9 through 14 show an alternative embodiment with a stop-plate 90 and 91 on the top portion 11 and bottom portion 13 of the cage 10, specifically the elongated sidewall 12 and elongated sidewall 16 towards the larger end wall 15, respectively. The stop-plate is configured to make contact with the top vertebrae and act as a guide to prevent from over rotation of the cage 10. Because the desired rotation of the cage 10 is 90 degrees the stop-plates 90 and 91 are oriented at right angles from the top portion 11 to prevent over rotation. The body of the stop-plates 90 and 91 are sloped, having a concave cross-section to promote easy transition when the cage is manipulated into position with sidewalls parallel to the longitudinal axis of the spine. Stop plates 90 and 91 can likewise be incorporated to each of the spinal cages 10 previously described. In this embodiment the cage 10 includes a bridging element 70 located on the top portion 11 and bridging element 72 located on the bottom portion 13. Bridging element 70, located on the top portion 11, traverses the hollow interior 30 and extends in a diagonal fashion from end 14 adjacent side wall 12 to end wall 15 adjacent side wall 16, as shown in FIG. 9. Bridging element 72, located on the bottom portion 13, traverses hollow interior 30 and extends in a diagonal fashion from end 14 adjacent side wall 16 to end wall 15 adjacent side wall 12, as shown in FIG. 15. Bridge members 70 and 72 are each provided with teeth that are in alignment with the teeth formed on the top and bottom peripheries of the elongated side walls 12 and 16. The profile of the teeth on the side walls 12 and 16 and bridging elements 70 and 72 that are in alignment have identical profiles.

The cage 10 may be constructed as a molded, cast or machined unitary structure or as a construct of components. The end walls and the sidewalls may be separate elements connected together by welding, adhesives, heat and pressure, or other fastening. The teeth may be integral with the sidewalls or separate pieces attached to the periphery of the sidewalls.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A spinal implant for stabilizing intervertebral space between adjacent vertebrae and maintaining curvature of the spine comprising a cage with a hollow interior and having a first end and a second end, a first elongated side connecting said first end and said second end, a second elongated side connecting said first end and said second end, said second elongated side diametrically opposed to said first elongated side about said hollow interior, said first elongated side and said second elongated side spaced apart forming an opening communicating with said hollow interior, said opening having a top and bottom periphery defined by the edges of said first elongated side and said second elongated side, said periphery including a plurality of angled teeth, a first portion of said plurality of teeth angled toward said first end and a second portion of said plurality of teeth angled away from said first end, and a first recess formed between said first portion of said plurality of teeth angled toward said first end and said second portion of said plurality of teeth angled away from said first end, said first recess extending to a location on either said first or second elongated wall a predetermined distance from said periphery and a second recess formed between said first portion of said plurality of teeth angled toward said first end and said second portion of said plurality of teeth angled away from said first end, said second recess extending to a location on said side wall a predetermined distance from said periphery wherein the first recess is formed on either the first or second elongated side, and the second recess is located on said elongated side opposite said first recess, the first recess is formed on either the top or bottom periphery and the second recess is located on the periphery opposite the first recess, said first recess and said second recess having an edge each having a sloped surface at approximately 45 degrees from the longitudinal centerline of said spinal implant.

2. The spinal implant according to claim 1 comprising said first elongated side and said second elongated side formed in an arc between said first end and said second end, said arc increasing said hollow interior of said cage.

3. The spinal implant according to claim 1 comprising a bone growth material disposed in said hollow interior, said bone growth material adapted to contact adjacent vertebrae through said opening.

4. The spinal implant according to claim 1 comprising said first end being longer than said second end, said first elongated side and said second elongated side extending toward each other to form a wedge, said wedge adapted to contact adjacent vertebrae to maintain curvature of the spine.

5. The spinal implant according to claim 4 comprising said first end having a rectilinear shape with two opposite long sides connected to two opposite short sides, said first elongated sidewall attached to one long side of said first end and said second elongated sidewall attached to a second long side of said first end.

6. The spinal implant according to claim 5 comprising said second end having a rectilinear shape with two opposite sides shorter than said opposite long sides of said first end, said first elongated sidewall attached to one shorter side of said second end and said second elongated sidewall attached to a the opposite shorter side of said second end.

7. The spinal implant according to claim 1 comprising at least two stop-plates located at right angles to said peripheral edge of said first elongated sidewall toward said second end and said peripheral edge of said second elongated sidewall toward said second end.

8. The spinal implant according to claim 1, wherein the cage includes a first bridging element located in either the top or bottom portion of said cage and extends between said first and second elongated side walls.

9. The spinal implant according to claim 8, wherein said cage includes a second bridging element located in the portion opposite the first bridging element and extends between said first and second elongated sides.

10. The spinal implant according to claim 9, wherein said first and second bridging element each include a plurality of angled teeth, a first portion of said plurality of teeth angled toward said first end and a second portion of said plurality of teeth angled away from said first end.

11. The spinal implant according to claim 8, wherein said bridging element includes a plurality of angled teeth, a first portion of said plurality of teeth angled toward said first end and a second portion of said plurality of teeth angled away from said first end.

12. The spinal implant according to claim 1, comprising at least one radiopaque marker in said cage.

13. The spinal implant according to claim 1, wherein the first and second end walls are configured to removeably receive an implant tool used to manipulate the implant for permanent positioning in the spine.

* * * * *